United States Patent [19]

Okawa et al.

[11] Patent Number: 5,262,555
[45] Date of Patent: Nov. 16, 1993

[54] METHOD FOR THE PREPARATION OF ACRYLOXY GROUP-CONTAINING OR METHACRYLOXY GROUP-CONTAINING ORGANOSILICON COMPOUNDS

[75] Inventors: Tadashi Okawa; Shuji Yamada, both of Chiba, Japan

[73] Assignee: Dow Corning Toray Silicone Co., Ltd., Tokyo, Japan

[21] Appl. No.: 30,900

[22] Filed: Mar. 15, 1993

[30] Foreign Application Priority Data

Mar. 25, 1992 [JP] Japan .................. 4-098921

[51] Int. Cl.$^5$ .................. C07F 7/08; C07F 7/18
[52] U.S. Cl. .................. 556/440
[58] Field of Search .................. 556/440

[56] References Cited

U.S. PATENT DOCUMENTS

| | | | |
|---|---|---|---|
| 3,258,477 | 6/1966 | Gueddemann | 260/448.8 |
| 4,709,067 | 11/1987 | Chu et al. | 556/440 |
| 4,780,555 | 10/1988 | Bank | 556/440 |
| 4,940,766 | 7/1990 | Gay et al. | 556/440 |
| 4,946,977 | 8/1990 | Bernhardt et al. | 556/440 |
| 5,103,032 | 4/1992 | Turner et al. | 556/440 X |
| 5,145,979 | 9/1992 | Takatsuna et al. | 556/440 |

FOREIGN PATENT DOCUMENTS 613466 11/1964 Belgium .
949126 11/1964 United Kingdom .

OTHER PUBLICATIONS

Polymer, 26, 1985: pp. 437-442.

*Primary Examiner*—Paul F. Shaver
*Attorney, Agent, or Firm*—Sharon K. Severance

[57] ABSTRACT

The instant invention pertains to a high-productivity, high-yield method for the preparation of acryloxy group-containing or methacryloxy group-containing organosilicon compounds. The method of the instant invention comprises an addition reaction, in the presence of a hydrosilylation-reaction catalyst, between (A) an ester of acrylic acid with aliphatic ally unsaturated alcohol or aliphatically unsaturated phenol; or (B) an ester of methacrylic acid with aliphatically unsaturated alcohol or aliphatically unsaturated phenol; and (C) a silicon compound that contains silicon-bonded hydrogen and by then distilling the reaction mixture in the presence of a metal halide.

12 Claims, No Drawings

METHOD FOR THE PREPARATION OF ACRYLOXY GROUP-CONTAINING OR METHACRYLOXY GROUP-CONTAINING ORGANOSILICON COMPOUNDS

BACKGROUND OF THE INVENTION

Acryloxy-containing organosilicon compounds or methacryloxy- containing organosilicon compounds (hereinafter referred to as (meth)acryloxy-containing organosilicon compounds) readily react with radical-polymerizing monomers such as methyl methacrylate and styrene and are therefore very useful as starting materials for copolymers deriving from these monomers and as modifiers of polymers produced from the aforesaid monomers.

Such (meth)acryloxy-containing organosilicon compounds are prepared by the addition reaction of SiH-containing organosilicon compounds with the corresponding (meth)acrylic acid esters of aliphatically unsaturated alcohols or aliphatically unsaturated phenols followed by isolation by distillative purification from the crude mixture as set forth in U.S. Pat. No. 3,258,477; Belgian Patent Number 613,466; and British Patent Number 949,126. However, distillative purification and isolation is highly problematic. Because (meth)acryloxy-containing organosilicon compounds of this type readily undergo radical polymerization in the presence of heat, the distillative purification step itself results in a radical-reaction-induced increase in degree of polymerization. As a result, it has been difficult to obtain highly pure (meth)acryloxy-containing organosilicon compounds in high yields. Accordingly, investigations have been carried out on the implementation of this distillative purification step by the addition to the aforesaid crude mixture of a polymerization inhibitor, for example, hindered phenols, amine compounds, quinone compounds, and so forth as set forth in Polymer, 26, 437, 1985, but these methods have not proven to be entirely satisfactory.

In the instant invention it has been discovered that specific metal halides provide exceptional stabilization of the crude mixture in the preparative method under consideration and actually prevent gelation during distillative purification. The present invention was achieved based on this finding.

It is an object of the present invention the introduction of a highly productive method for the high-yield preparation of (meth)acryloxy-containing organosilicon compounds.

THE INVENTION

The present invention relates to a method for the preparation of acryloxy group-containing or methacryloxy group-containing organosilicon compounds (hereinafter referred to as (meth)acryloxy-containing organosilicon compounds), wherein said method is characterized by the execution of an addition reaction, in the presence of a hydrosilylation-reaction catalyst, between (A) an ester of acrylic acid with aliphatically unsaturated alcohol or aliphatically unsaturated phenol; or (B) an ester of methacrylic acid with aliphatically unsaturated alcohol or aliphatically unsaturated phenol; and (C) a silicon compound that contains silicon-bonded hydrogen; and by then distilling the reaction mixture in the presence of a metal halide.

Component (A) of the present invention is an ester of acrylic acid with aliphatically unsaturated alcohol or aliphatically unsaturated phenol. Component (A) may be exemplified by, but not limited to, allyl acrylate, hexenyl acrylate, allyloxyethyl acrylate, and styryl acrylate.

Component (B) is the ester of methacrylic acid with aliphatically unsaturated alcohol or aliphatically unsaturated phenol. Component (B) may be exemplified by, but not limited to allyl methacrylate, hexenyl methacrylate, allyloxyethyl methacrylate, and styryl methacrylate.

Component (C) of the present invention is a SiH-containing silicon compounds. Component (C) may be methyldichlorosilane, dimethylchlorosilane, trimethoxysilane, methyldimethoxysilane, dimethylmethoxysilane, pentamethyldisiloxane, and 1,1,2,2- tetramethyldisiloxane.

The hydrosilylation-reaction catalyst employed by the present invention is preferably a transition metal complex catalyst in which the transition metal is from Group VIII of the Periodic Table, and most preferably is a platinum group metal catalyst. Such catalysts may be exemplified by, but not limited to, alcohol solutions of chloroplatinic acid, olefin complexes of platinum, and complexes between platinum and vinyl-containing siloxane.

The (meth)acryloxy-containing organosilicon compounds of the instant invention are produced by the addition-reaction of the ester of (meth)acrylic acid with aliphatically unsaturated alcohol or aliphatically unsaturated phenol with the SiH-containing organosilicon compound in the presence of the hydrosilylation-reaction catalyst. This reaction can be carried out without solvent or in the presence of solvent. Useable solvents may be exemplified by aromatic hydrocarbons such as benzene, toluene, xylene, and others; aliphatic hydrocarbons such as hexane, heptane, and others; ethers such as tetrahydrofuran, diethyl ether, and others; ketones such as acetone, methyl ethyl ketone, and others; and esters such as ethyl acetate, butyl acetate, and others.

The method of the present invention can be carried out at room temperature, but in order to obtain a satisfactory reaction rate it is preferable to carry out the reaction at temperatures of at least 30° C. Since the (meth)acryloxy group is prone to polymerize at high temperatures, resulting in gelation, the reaction temperature should generally be 30° C. to 100° C. and preferably is 40° C. to 60° C.

In the method of the present invention, the reaction mixture obtained in the manner described above is distilled in the presence of metal halide. Metal halide useful in the present invention may be exemplified by the chlorides, bromides, and iodides of chromium, cobalt, nickel, germanium, zinc, tin, mercury, copper, iron, palladium, tungsten, silver, vanadium, molybdenum, ruthenium, platinum, antimony, bismuth, selenium, and tellurium. The metal halide should be added at 0.01 to 10 weight% referred to the total weight of the reaction mixture. Furthermore, the distillation process under consideration may be carried out by known distillation methods, but distillation under reduced pressure is ordinarily used.

So that those skilled in the art can understand and appreciate the invention taught herein, the following examples are presented, being it understood that these examples should not be used to limit the scope of this invention found in the claims attached hereto. In the examples, "%" denotes weight%.

EXAMPLE 1

Dimethylchlorosilane (236.5 g. 2.5 mol), allyl methacrylate (315.4 g, 2.5 mol), and phenothiazine (2.5 g) were introduced into a stirrer-equipped four-necked flask and mixed with a chloroplatinic acid/1,2-divinyltetramethyldisiloxane complex added in a quantity corresponding to 5 ppm as weight of platinum metal relative to the total weight of the starting materials introduced. This mixture was then stirred and heated to 50° C. After confirmation that the addition reaction had commenced, the reaction was carried out by stirring for 2 hours while controlling the temperature at 50° C. by means of water or air cooling. When the reaction mixture was analyzed by gas-liquid chromatography (GLC), the crude reaction mixture was found to contain 75 weight% methacryloxypropyldimethylchlorosilane. After this reaction mixture had been stripped of low boilers in vacuo at room temperature, copper (II) chloride (8.3 g, 61.7 mmol) was added with mixing. This mixture was subsequently distilled under reduced pressure at 7 mmHg, and the fraction at 100 to 115° C. was collected. The yield of this fraction was 384.6 g (69.7% yield). This fraction was methacryloxypropyldimethylchlorosilane with a purity of 97.6% according to GLC.

EXAMPLE 2

The reaction was carried on a scale twice that in Example 1. and a crude reaction mixture containing 74 weight% methacryloxypropyldimethylchlorosilane was obtained. After this reaction mixture had been stripped of low boilers in vacuo at room temperature, copper (II) chloride (16.6 g, 123.4 mmol) was added to the reaction mixture. Distillation was conducted under reduced pressure at 5 mmHg, and the fraction at 100° to 120° C. was collected. The yield of this fraction was 777.1 g (70.4% yield). According to GLC the purity of this fraction was 97.5%.

EXAMPLE 3

A crude reaction mixture containing 75 weight% methacryloxypropyldimethylchlorosilane was prepared as in Example 1. Into respective 20 g portions of this crude reaction mixture was introduced 5.3 mmol of each metal halide reported in Table 1, followed by stirring while heating at 60° C. 0.1 g samples were withdrawn at regular time intervals. Each 0.1 g sample was introduced into 2 g hexane and examined with the naked eye for any polymer-derived precipitate. For comparison, this same evaluation was also carried out on the crude reaction mixture containing 75% methacryloxypropyldimethylchlorosilane without any addition of metal halide. The results are reported in Table 1.

In the instances of metal halide addition, there was absolutely no observation of polymer-derived precipitate even after stirring and heating for 7 hours.

On the other hand, in the case of the comparison example in which crude reaction mixture from the same batch was evaluated under identical conditions but without the addition of metal halide, polymer-derived precipitation was observed as early as 1 hour, and the quantity of precipitate increased with time until after 7 hours there was complete loss of fluidity and gelation had occurred.

TABLE 1

| Metal Halide | Results Observed After 7 Hours |
|---|---|
| $CrCl_3$ | no polymer production |
| $VCl_4$ | no polymer production |
| $CoCl_2$ | no polymer production |
| $MoCl_5$ | no polymer production |
| $NiCl_2$ | no polymer production |
| $RuCl_2$ | no polymer production |
| $GeCl_4$ | no polymer production |
| $PtCl_4$ | no polymer production |
| $ZnCl_2$ | no polymer production |
| $SbCl_3$ | no polymer production |
| $SnCl_4$ | no polymer production |
| $BiCl_3$ | no polymer production |
| $HgCl_2$ | no polymer production |
| $SeCl_4$ | no polymer production |
| $CuCl_2$ | no polymer production |
| $TeCl_4$ | no polymer production |
| $FeCl_3$ | no polymer production |
| $PdCl_2$ | no polymer production |
| $WCl_6$ | no polymer production |
| $AgCl$ | no polymer production |
| no addition (comparison example) | polymer is produced (gelation occurred) |

The method of the present invention has the characteristic that the polymerization of reaction product that may occur during distillative purification can be prevented and (meth)acryloxy containing organosilicon compounds can therefore be prepared in high yields at high productivities.

What is claimed is:

1. A method for the preparation of acryloxy group-containing and methacryloxy group-containing organosilicon compounds, wherein the method comprises
    (I) reacting, in the presence of a hydrosilylation-reaction catalyst,
        (A) an ester of acrylic or methacrylic acid selected from the group consisting of an ester of acrylic acid with aliphatically unsaturated alcohol, an ester of an acrylic acid with aliphatically unsaturated phenol, an ester of methacrylic acid with aliphatically unsaturated alcohol and an ester of methacrylic acid with aliphatically unsaturated phenol; and
        (B) a silicon compound that contains silicon-bonded hydrogen; and
    (II) distilling the reaction mixture of (I) in the presence of a metal halide selected from the group consisting of chromium chloride, cobalt chloride, nickel chloride, germanium chloride, zing chloride, tin chloride, mercury chloride, copper chloride, iron chloride, palladium chloride, tungsten chloride, silver chloride, vanadium chloride, molybdenum chloride, ruthenium chloride, platinum chloride, antimony chloride, bismuth chloride, selenium chloride, and tellurium chloride.

2. The method as claimed in claim 1 wherein metal halide is copper chloride.

3. The method as claimed in claim 1 wherein (A) is an ester of an acrylic acid with aliphatically unsaturated alcohol.

4. The method as claimed in claim 1 wherein (A) is an ester of an acrylic acid with aliphatically unsaturated phenol.

5. The method as claimed in claim 1 wherein (A) is an ester of methacrylic acid with aliphatically unsaturated alcohol.

6. The method as claimed in claim 1 wherein (A) is an ester of methacrylic acid with aliphatically unsaturated phenol.

7. The method as claimed in claim 1 wherein (A) is allyl methacrylate.

8. The method as claimed in claim 1 wherein (B) is dimethylchlorosilane.

9. The method as claimed in claim 1 wherein the hydrosilylation-reaction catalyst is a transition metal complex catalyst where the transition metal is selected from a Group VIII of the periodic table.

10. The method as claimed in claim 9 wherein the hydrosilylation-reaction catalyst is a chloroplatinic acid/1,2 divinyltetramethyldisloxane complex.

11. The method as claimed in claim 1 wherein the distillation is conducted under reduced pressure.

12. The method as claimed in claim 1 wherein the reaction is carried out additionally in the presence of a solvent.

* * * * *

REEXAMINATION CERTIFICATE (2408th)

United States Patent [19]

Okawa et al.

[11] B1 5,262,555

[45] Certificate Issued    Oct. 4, 1994

[54] METHOD FOR THE PREPARATION OF ACRYLOXY GROUP-CONTAINING OR METHACRYLOXY GROUP-CONTAINING ORGANOSILICON COMPOUNDS

[75] Inventors: Tadashi Okawa; Shuji Yamada, both of Chiba, Japan

[73] Assignee: Dow Corning Toray Silicone Company, Limited, Tokyo, Japan

Reexamination Request:
No. 90/003,370, Mar. 25, 1994

Reexamination Certificate for:
Patent No.: 5,262,555
Issued: Nov. 16, 1993
Appl. No.: 30,900
Filed: Mar. 15, 1993

[30] Foreign Application Priority Data

Mar. 25, 1992 [JP]   Japan ................... 4-098921

[51] Int. Cl.$^5$ .................... C07F 7/08; C07F 7/18
[52] U.S. Cl. .................................... 556/440
[58] Field of Search ........................... 556/440

[56] References Cited

U.S. PATENT DOCUMENTS

| | | | |
|---|---|---|---|
| 3,258,477 | 6/1966 | Plueddemann | 556/440 X |
| 4,709,067 | 11/1987 | Chu et al. | 556/440 |
| 4,780,555 | 10/1988 | Bank | 556/440 |
| 4,940,766 | 7/1990 | Gay et al. | 556/440 |
| 4,946,977 | 8/1990 | Bernhardt et al. | 556/440 |
| 5,103,032 | 4/1992 | Turner et al. | 556/440 X |
| 5,145,979 | 9/1992 | Takatsuna et al. | 556/440 |

FOREIGN PATENT DOCUMENTS

| | | |
|---|---|---|
| 613466 | 11/1964 | Belgium . |
| 949126 | 11/1964 | United Kingdom . |

OTHER PUBLICATIONS

Chemical Abstracts, vol. 97, No. 18, Nov. 1982, #145329b, Barabashina et al.
*Polymer*, 26, 1985, pp. 437–442.
Chemical Abstracts, vol. 83, No. 8, Aug. 1975, #59753q, Kouril.
Chemical Abstracts, vol. 100, No. 20, May 1984, #157,059g, Barabashina et al.
Chemical Abstracts, vol. 77, No. 2, Oct. 1972, #5987b, Bengough et al.

*Primary Examiner*—Paul F. Shaver

[57] ABSTRACT

The instant invention pertains to a high-productivity, high-yield method for the preparation of acryloxy group-containing or methacryloxy group-containing organosilicon compounds. The method of the instant invention comprises an addition reaction, in the presence of a hydrosilylation-reaction catalyst, between (A) an ester of acrylic acid with aliphatic ally unsaturated alcohol or aliphatically unsaturated phenol; or (B) an ester of methacrylic acid with aliphatically unsaturated alcohol or aliphatically unsaturated phenol; and (C) a silicon compound that contains silicon-bonded hydrogen and by then distilling the reaction mixture in the presence of a metal halide.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION IT HAS BEEN DETERMINED THAT:

Claim 2 is cancelled.

Claim 1 is determined to be patentable as amended.

Claims 3 to 12, dependent on an amended claim, are determined to be patentable.

1. A method for the preparation of acryloxy group-containing and methacryloxy group-containing organosilicon compounds, wherein the method comprises
   (I) reacting, in the presence of a hydrosilylation-reaction catalyst,
      (A) an ester of acrylic or methacrylic acid selected from the group consisting of an ester of acylic acid with aliphatically unsaturated alcohol, an ester of an acrylic acid with aliphatically unsaturated phenol, an ester of methacrylic acid with aliphatically unsaturated alcohol and an ester of methacrylic acid with aliphatically unsaturated phenol; and
      (B) a silicon compound that contains silicon-bonded hydrogen; and
   (II) distilling the reaction mixture of (I) in the presence of a metal halide selected from the group consisting of chromium chloride, cobalt chloride, nickel chloride, germanium chloride, zinc chloride, tin chloride, mercury chloride, [copper chloride,] iron chloride, palladium chloride, tungsten chloride, silver chloride, vanadium chloride, molybdenum chloride, ruthenium chloride, platinum chloride, antimony chloride, bismuth chloride, selenium chloride, and tellurium chloride.

* * * * *